(12) United States Patent
Mongeon

(10) Patent No.: US 7,878,201 B2
(45) Date of Patent: Feb. 1, 2011

(54) SUPRAGLOTTIC AIRWAY DEVICE AND METHOD OF USE

(76) Inventor: Douglas R. Mongeon, 11201 Meads Ave., Orange, CA (US) 92869

( * ) Notice: Subject to any disclaimer, the term of this patent is extended or adjusted under 35 U.S.C. 154(b) by 1069 days.

(21) Appl. No.: 11/529,846

(22) Filed: Sep. 29, 2006

(65) Prior Publication Data

US 2008/0078402 A1  Apr. 3, 2008

(51) Int. Cl.
*A61M 16/00* (2006.01)
(52) U.S. Cl. .............. 128/207.15; 128/207.14; 128/204.18; 128/200.26; 600/207; 604/96.01
(58) Field of Classification Search .......... 128/200.26, 128/204.18, 207.14–207.17; 604/96.01; 606/190–200; 600/201, 204, 207
See application file for complete search history.

(56) References Cited

U.S. PATENT DOCUMENTS

| | | | | |
|---|---|---|---|---|
| 3,658,058 | A * | 4/1972 | Neidhart et al. | 128/201.18 |
| 3,821,957 | A * | 7/1974 | Riely et al. | 604/178 |
| 3,924,636 | A * | 12/1975 | Addison | 128/206.25 |
| 3,948,273 | A | 4/1976 | Sanders | |
| 4,170,232 | A | 10/1979 | Khoury | |
| 4,249,529 | A * | 2/1981 | Nestor et al. | 128/207.17 |
| 5,033,466 | A | 7/1991 | Weymuller, Jr. | |
| 5,322,088 | A * | 6/1994 | Sampers et al. | 139/1 R |
| 5,507,535 | A * | 4/1996 | McKamey et al. | 285/149.1 |
| 5,918,598 | A | 7/1999 | Belfer et al. | |
| 5,937,861 | A | 8/1999 | Augustine | |
| 5,988,167 | A | 11/1999 | Kamen | |
| 6,012,452 | A | 1/2000 | Pagan | |
| 6,070,581 | A * | 6/2000 | Augustine et al. | 128/207.15 |
| 6,079,409 | A | 6/2000 | Brain | |
| 6,119,695 | A | 9/2000 | Augustine et al. | |
| 6,196,223 | B1 | 3/2001 | Belfer et al. | |
| 6,318,367 | B1 | 11/2001 | Mongeon | |
| 6,338,343 | B1 | 1/2002 | Augustine et al. | |
| 6,390,093 | B1 | 5/2002 | Mongeon | |
| 6,427,686 | B2 | 8/2002 | Augustine et al. | |
| 6,561,192 | B2 * | 5/2003 | Palmer | 128/207.17 |
| 6,568,388 | B2 * | 5/2003 | Christopher | 128/200.26 |
| 6,604,525 | B2 | 8/2003 | Pagan | |
| 6,609,521 | B1 * | 8/2003 | Belani et al. | 128/207.14 |
| 6,655,384 | B2 * | 12/2003 | Antenbring et al. | 128/207.14 |

(Continued)

OTHER PUBLICATIONS

U.S. Appl. No. 10/985,935, Jul. 14, 2005, Koyama, et al.

*Primary Examiner*—Kevin C Sirmons
*Assistant Examiner*—Clinton Ostrup
(74) *Attorney, Agent, or Firm*—Mind Law Firm; Jeromye V. Sartain; Justin G. Sanders

(57) ABSTRACT

A supraglottic airway device comprising a tube and a face plate assembly slidably installed on the tube, whereby upon insertion of the tube within the airway of a patient the face plate assembly is slid distally along the tube so as to substantially seal about the mouth of the patient. The supraglottic airway device further comprises an introduction tip assembly mounted on the tube substantially opposite the face plate assembly so as to guide the device into the patient airway and an expandable foam cuff located along the tube between the face plate assembly and the tip assembly so as to seat the device within the airway. The face plate assembly may further comprise tabs for substantially sealing within the nose of the patient.

7 Claims, 12 Drawing Sheets

U.S. PATENT DOCUMENTS

| | | |
|---|---|---|
| 6,729,325 B2 | 5/2004 | Alfery |
| 6,745,773 B1 | 6/2004 | Gobel |
| 6,830,049 B2 | 12/2004 | Augustine et al. |
| 2003/0192552 A1* | 10/2003 | Mongeon ............... 128/207.14 |
| 2004/0194785 A1* | 10/2004 | Miller ................... 128/207.14 |

* cited by examiner

SUPRAGLOTTIC AIRWAY DEVICE AND METHOD OF USE

BACKGROUND OF THE INVENTION

1. Incorporation by Reference

Applicant hereby incorporates herein by reference any and all U.S. patents and U.S. patent applications cited or referred to in this application.

2. Field of the Invention

Aspects of this invention relate generally to artificial airway devices, and more particularly to supraglottic airway devices for seating within and/or sealing a patient's airway so as to enable spontaneous or positive-pressure ventilation.

3. Description of Related Art

The following art defines the present state of this field:

U.S. Pat. No. 3,924,636 to Addison is directed to an endotracheal tube holder for holding an endotracheal tube in a patient's mouth during surgery. The tube holder comprises a flexible, adhesive-backed strip adapted to be secured over the mouth of the patient. The strip is provided with a central opening through which the endotracheal tube can be inserted, and a holding strap having releasable, self-adhering ends is mounted on the strip adjacent the opening. When the endotracheal tube is properly positioned, the holding strap is wrapped securely about the tube and fastened to itself to hold the tube in place.

U.S. Pat. No. 3,948,273 to Sanders is directed to an endotracheal or tracheostomy tube having a non-sticking inside surface for allowing for the free movement of a suction catheter through the tube. The non-sticking surface is in the form of a series of grooves separated by ridges having thin edges extending through the length of the tube for engaging the surface of the catheter.

U.S. Pat. No. 4,170,232 to Khoury is directed to a tracheobronchial sampler device comprising a tubular member insertable into a chest tube and defining a passage through which a sampling catheter can be passed when the chest tube is inserted into the trachea of a patient, in which means are provided for spacing the passage of said tubular member away from the inner wall of said chest tube, as well as stop means for preventing the insertion of the tubular member through the chest tube beyond a predetermined point. The device enables a sample to be obtained from the desired tracheal region without undesired contamination as the sampling catheter is inserted into the patient.

U.S. Pat. No. 5,033,466 to Weymuller, Jr. is directed to an improved double-cuffed endotracheal tube designed for insertion through the mouth of a patient to provide a passage for artificial respiration. The device includes an elongated flexible tube having proximal and distal end portions, the distal end portion designed for insertion into a patient and the proximal end portion capable of connection to an artificial respirator. The tube includes a lower inflatable-deflatable cuff located above the distal end portion and secured to and encircling the tube. When properly positioned and inflated, the lower cuff sealingly engages the inner wall of the trachea below the larynx and prevents secretions from traveling into the upper trachea or larynx. The tube also includes an upper inflatable-deflatable foam-filled cuff secured to and encircling the tube above the lower cuff. The upper cuff is located on the tube at a predetermined point for positioning in the larynx between the vocal cords and cricoarytenoid joint. When properly positioned, the upper cuff extends equal distances above and below the glottis, and upon expansion or inflation, engages the interior surfaces of the larynx, preventing contact of the tube with those surfaces. The upper foam-filled cuff is designed to provide a sufficiently large area of contact between the cuff and laryngeal tissues to evenly distribute the pressure exerted by the endotracheal tube throughout the cuff, and protects the laryngeal tissues from injuries commonly caused by prolonged intubation of conventional endotracheal tubes.

U.S. Pat. No. 5,918,598 to Belfer et al. is directed to a strapless respiratory facial mask for attachment to the wearer's face including a mask having a central section and three edges forming a generally triangular configuration for covering and surrounding the nose of the wearer; wherein the first and second edges of the mask extend along the opposite sides of the nose of the wearer, and the third edge extends across the upper lip area of the wearer. The central section of the mask is formed of a thermoplastic material and has a first central opening formed therein for making an external connection to the mask, and having a second central opening below the first central opening and an external tubular section connected to the second central opening for making a connection to a gas supply. The mask further includes an elastic and moldable cushioning material connected to the first, second and third edges of the mask to form a peripheral sealing section for engaging the facial contours and skin of the wearer's face. The peripheral sealing section includes first, second and third sealing section edges. In addition, the mask also includes a plurality of sealing strips formed of the cushioning material for attachment to one or more of the first, second or third sealing section edges for providing an increased sealing area for the mask.

U.S. Pat. No. 5,937,861 to Augustine is directed to an endotracheal or tracheostomy tube with a self-inflating cuff near its distal end including one or more resilient, compressible support parts within the cuff for exerting a low sealing pressure against a trachea during expiration.

U.S. Pat. No. 5,988,167 to Kamen is directed to an artificial airway provided for permitting medical personnel access to a patient's airway. The artificial airway includes a foam cuff laryngeal mask having an air tube, a pilot tube, and a laryngeal mask. The air tube and the laryngeal mask cooperate to form a gas passage that permits gases to flow through the foam cuff laryngeal mask. The laryngeal mask includes a foam cuff having a pliable sheath filled with a resilient material. Air is drawn out of the resilient material through the pilot tube which causes the foam cuff to deflate. The foam cuff laryngeal mask is then inserted into the patient's airway and positioned over the larynx. Air is allowed to enter the pilot tube and the resilient material expands so that the foam cuff forms a substantial seal with the larynx.

U.S. Pat. No. 6,012,452 to Pagan is directed to a laryngeal mask airway having a foam cuff formed on the patient surface of a plate attached at the patient end of a tube. The cuff is of a self-skinning foam so that the skin of the foam forms the outer surface of the cuff and seals with the plate. An air lumen extruded along the tube opens at one end into the interior of the cuff and at the other end connects with an air line. The cuff can be compressed for insertion and removal by applying suction to the air line.

U.S. Pat. No. 6,079,409 to Brain is directed to an intubating LMA construction featuring a rigid airway tube wherein curvature in a single plane establishes essentially an arcuate path of angular extent in the preferred range of 130 degrees, plus or minus 5 degrees, which has been found to be in substantial anatomical conformance with the adult human's airway path, between a proximal end of the arc at substantial register with the longitudinal midpoint of the hard palate, and a distal end that faces and is at short offset from the glottic aperture, it being understood that these findings apply to suitably quantified allowance for variations in patient-head anatomy, as is for example customary for different sizes of LMA devices, each of which is adapted to serve one of five selected patient-size ranges. The proximal end of the rigid tube is suitably a short straight portion which is tangentially and integrally related to the proximal end of the arc. And the distal end of the arc is fitted with flexible mask structure of preferably elastomeric material such as silicone rubber, wherein an internal ramp formation within the mask structure assures a limited but important measure of further and stabilized guidance of an ET which has emerged from the distal end of the rigid tube, such that unguided displacement of the ET (i.e., beyond the ramp) is oriented to target safe entry of the ET into the glottic opening.

U.S. Pat. Nos. 6,119,695 and 6,338,343 to Augustine et al. are directed to an airway device for sealing against the laryngeal opening including an air tube with proximal and distal ends and a sealing member attached to the distal end. The sealing member has a distal portion with a pair of opposing lateral flanges for engaging the cricoid cartilage to laterally align the sealing member with respect to the laryngeal inlet. The sealing member has a compressible anterior surface that contacts and seals against the laryngeal inlet. A tubular extension of the distal end of the air tube projects through and beyond the compressible anterior surface. The sealing member has a pronounced sigmoid shape having a lower section which, together with the tubular extension, creates a hook that provides an end point for accurate cephalad-caudad depth placement of the sealing member against the rim of the laryngeal inlet.

U.S. Pat. No. 6,196,223 to Belfer et al. is directed to a strapless respiratory facial mask for attachment to the wearer's face including a moldable laminated gasket member having a cushioning layer and an adhesive layer for engaging the facial contours and skin of the wearer's face; and the gasket member having a central opening for receiving the nose of the wearer. The facial mask further includes a nose piece member having a central section and three edges forming a generally triangular configuration for covering and surrounding the nose of the wearer. The central section of the nose piece member also includes a first opening for connecting to a gas supply; and the nose piece member is adhered along its three edges to the cushioning layer on the gasket member to form a peripheral seal. The central section of the nose piece member has a contoured shape for receiving the wearer's nose therein.

U.S. Pat. No. 6,318,367 to Mongeon is directed to an artificial airway device (also known as a Laryngeal Mask Assembly, "LMA," or Disposable Laryngeal Mask Assembly, "DLMA") used to facilitate lung ventilation in an unconscious patient and methods for using an artificial airway device. The device includes a curved but flexible airway tube and a hollow mask support at one end of the airway tube. The mask support includes a fairly rigid support base and a flexible, generally annular peripheral skirt which is attached to the support base. A distal tip of the mask support is narrowed and projects outwardly, thereby providing a nose portion which is used to easily locate the distal tip of the mask in the entrance into the esophagus. The skirt is capable of conforming to the space behind the larynx so as to form a seal around the circumference of the laryngeal inlet without penetrating into the interior of the larynx. The skirt surrounds a hollow interior space or lumen of the mask base into which the airway tube opens. During insertion of the LMA into the patient, the skirt is contracted, to make the LMA easier to insert into the patient's airway. The skirt of the mask can be selectively manipulated, e.g. expanded, to improve the sealing contact with the tissues around the circumference of the laryngeal inlet. The skirt, when expanded, and the support base form a "cup-like" shape, which enhances the stabilization and sealing of the mask in the airway.

U.S. Pat. No. 6,390,093 to Mongeon is directed to an artificial airway device used to facilitate lung ventilation in an unconscious patient, and methods for using and inserting an artificial airway device. The device includes a curved but flexible airway tube and a mask portion. A mask opening portion is shaped so as to fit closely adjacent and closely over the patient's laryngeal opening. A seating tip includes a series of thin, flexible fins or gills which project from a finger portion extending from the mask opening portion. The fins or gills seat against the pharyngeal side of the cricoid, just above the esophagus. The mask portion can be anchored against a relatively hard surface without causing damage to delicate tissue in the esophagus. The seating tip provides a reference for the person inserting the artificial airway device which ensures that the mask portion is properly in place and adequately anchored. The artificial airway also includes an inflatable cuff used to anchor the artificial airway in place.

U.S. Pat. Nos. 6,427,686 and 6,830,049 to Augustine et al. are directed to a laryngeal airway device for sealing against the laryngeal opening including an air tube with proximal and distal ends and a sealing member attached to the distal end. The sealing member includes a coupler for coupling the device to an introducer. Complementing the laryngeal airway device is an introducer that includes a track for receiving the coupler of the laryngeal airway device and guiding the sealing member to a sealing position with respect to the laryngeal inlet. The introducer may include an epiglottic engager on a distal end to engage the epiglottis and retain it while the sealing member is being tracked to engagement with the laryngeal inlet.

U.S. Pat. No. 6,604,525 to Pagan is directed to the mask of a laryngeal mask assembly having a mount and an integral cuff at the patient end of a tube. The mount is of a thermoplastic material and the cuff is made by blow moulding from the material of the mount. A separate retaining plate seals an edge of the cuff with the mount and traps an inflation tube extending from the cuff to the inflation line of the tube.

U.S. Pat. No. 6,729,325 to Alfery is directed to an oral airway (510) including an elongate tubular member (512) having a distal (510) and a proximal end (514), the oral airway being configured to place the distal end in a supraglottic position when operatively placed within the hypopharynx of a patient. A temperature sensor (554) is operatively associated with the elongate tubular member to detect a core temperature of a patient with the distal end of the oral airway operatively placed in a superglottic position within the hypopharynx of the patient.

U.S. Pat. No. 6,745,773 to Gobel is directed to a tracheal tube by which the trachea is closed watertight by a fixation cuff blocking the trachea below the glottis, through which a ventilation cannula passes, and, situated cranially to it, above the cuff, a tampon-bladder made of flexible material expansible through the influx of fluid, which when filled differs in shape from the shape of the cuff, representing an improvement by means of which a patient could be intubated in the gentlest way over a long period with minimal risk of infection. In the invention this is accomplished by situating the tampon-bladder immediately against the cuff and constructing it of foil-like material and so designing it that when fully distended in size it fills the subglottal space.

U.S. patent application Ser. No. 10/985,935 to Koyama et al. is directed to an oral airway, which is used by being inserted into the mouth of a patient who is suffering from unconsciousness or has lost consciousness to secure an airway of the patient, adapted to be used with a tube to be inserted into the trachea of the patient through the mouth thereof. The oral air way includes a main body, and an insertion part provided on the main body. The insertion part is adapted to be inserted into the trachea of the patient through the mouth thereof so that an appropriate portion of the insertion part at the side of the distal end thereof comes into contact with the root of the tongue of the patient to secure the airway of the patient. The insertion part includes a guide groove for guiding the tube when the tube is inserted into the trachea of the patient, and the guide groove has a structure from which the tube can be separated after the distal end of the tube has been inserted into the trachea of the patient.

The prior art described above teaches an endotracheal tube holder, an endotracheal tube having a non-sticking inner surface, a tracheo-bronchial sampler device, a double-cuffed endotracheal tube, a strapless respiratory facial mask for customizing to the wearer's face, a tracheal tube with self-supporting tracheal tube cuff, a foam cuff for a laryngeal mask airway, laryngeal mask assemblies, an intubating laryngeal mask, an airway device with provision for lateral alignment, depth positioning, and retention in an airway, an artificial airway device and method of its use, an airway device with provision for coupling to an introducer, laryngeal mask airways and their manufacture, a perilaryngeal oral airway, a tracheal tube, and an oral airway and airway management assistive device provided with the oral airway, but does not teach a supraglottic airway device having a slidable face plate for sealing around the mouth, a reinforced foam tip for insertion within the hypopharynx or cricopharynx, or an expanding foam cuff for seating and sealing within the oropharynx or nasopharynx. Aspects of the present invention fulfill these needs and provide further related advantages as described in the following summary.

SUMMARY OF THE INVENTION

Aspects of the present invention teach certain benefits in construction and use which give rise to the exemplary advantages described below.

In a first aspect of the present invention, the supraglottic airway device comprises a tube and a face plate assembly slidably installed on the tube, whereby upon insertion of the tube within the airway of a patient the face plate assembly is slid distally along the tube so as to substantially seal about the mouth of the patient.

In another aspect of the invention, the supraglottic airway device comprises, in addition to the tube and the face plate assembly, an introduction tip assembly mounted on the tube substantially opposite the face plate assembly, whereby the introduction tip assembly guides the device into the patient airway and substantially locates within the hypopharynx.

In yet another aspect of the invention, the tube of the supraglottic airway is formed with an interior lumen, and the introduction tip assembly comprises a mounting portion connected to the tube and having an opening therein configured to communicate with the lumen. The introduction tip assembly further comprises a frame portion extending substantially distally from the mounting portion and having a foam insert installed thereon, whereby the frame portion substantially seats within the cricopharynx and the foam insert thereof absorbs bodily secretions.

In still another aspect of the invention, the supraglottic airway device comprises an expandable foam cuff mounted on the tube substantially between the face plate assembly and the introduction tip assembly so as to seat within the pharynx when the device is placed within the airway of a patient, whereby the cuff substantially seals the airway and seats and locates the device within the airway.

In yet another aspect of the invention, the supraglottic airway device comprises a face plate assembly further configured with tabs substantially corresponding to the nostrils of the patient, whereby upon distal advancement of the face plate assembly along the tube the tabs substantially seal the nose of the patient.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

DETAILED DESCRIPTION OF THE INVENTION

The above described drawing figures illustrate aspects of the invention in at least one of its exemplary embodiments, which are further defined in detail in the following description.

In the art of establishing a patient airway, known as "intubation," numerous devices have been implemented previously, including endotracheal tubes that are passed directly into the trachea and there establish a seal, usually through an inflatable cuff, and laryngeal airways that actually seat in or above the upper esophageal sphincter, or cricopharynx region, so as to block gastric reflux while effectively sealing off the pharynx and providing a guide path down the center of the laryngeal airway through which a secondary device such as an endotracheal tube can then be securely and safely passed into the trachea. The present invention is directed to a novel apparatus and method for achieving such an intubation relatively more safely and effectively.

Figure 1:
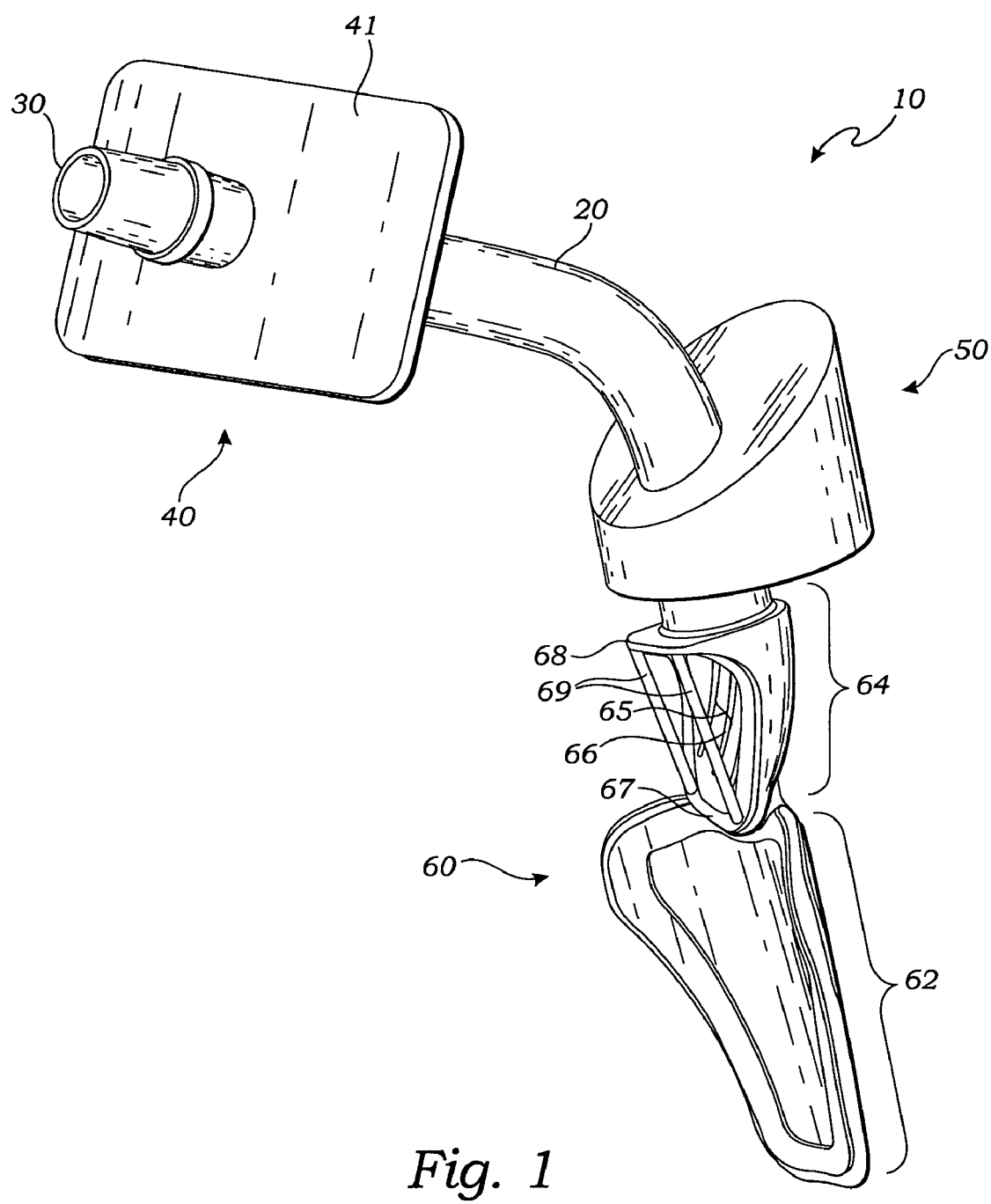
FIG. 1 is a front perspective view of an exemplary embodiment of the invention.

Turning first to FIG. 1, there is shown a perspective view of an exemplary supraglottic airway device 10 according to aspects of the present invention. The device 10 generally includes a tube 20 having a standard 15 mm connector 30 and a slidable face plate assembly 40 substantially at its proximal end and a foam cuff 50 and introduction tip assembly 60 substantially at its opposite distal end. The device 10 is sized and configured such that in use, as explained in more detail below in connection with FIGS. 10 and 11, the curvature of the tube 20 and configuration of the tip assembly 60 allow the "arrowhead" lower frame portion 62 of the tip assembly 60 upon insertion of the device 10 in the airway of a patient to be positioned within the upper esophageal sphincter or cricopharynx C, whereby the opening 66 formed in the mounting portion 64 of the tip 60 is positioned adjacent the opening to the larynx L while the foam cuff 50 upon expansion substantially seals the pharynx P. The lip 68 on the mounting portion 64 just over the opening 66 serves to hold the epiglottis E up and out of the way for clear access to the trachea T. Once the device 10 is so inserted, the face plate assembly 40 may be slidably advanced distally along the tube 20 so as to bring it into contact with the patient's mouth M, thereby further sealing off the airway.

Figure 2:
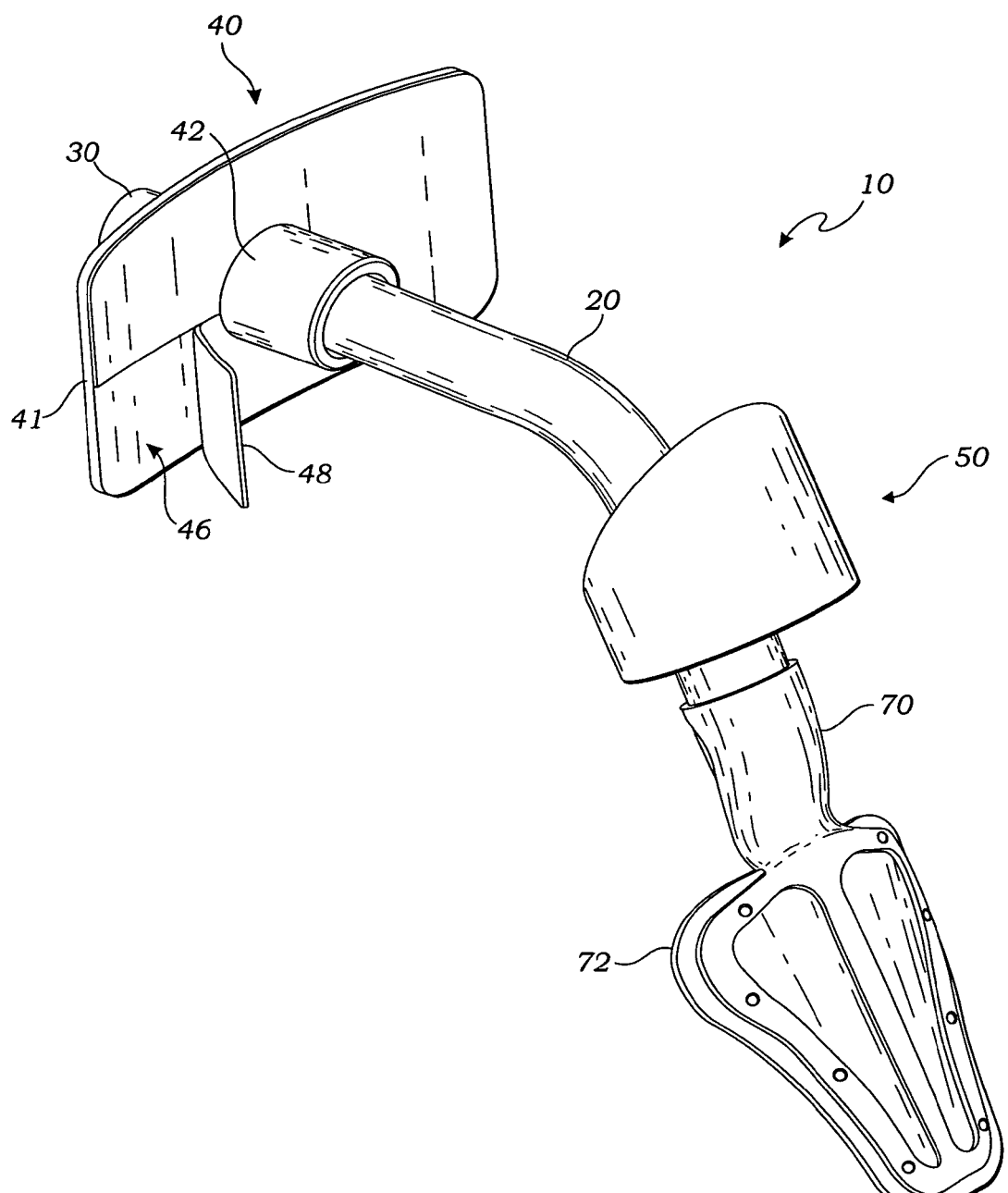
FIG. 2 is a back perspective view thereof.
Figure 3:
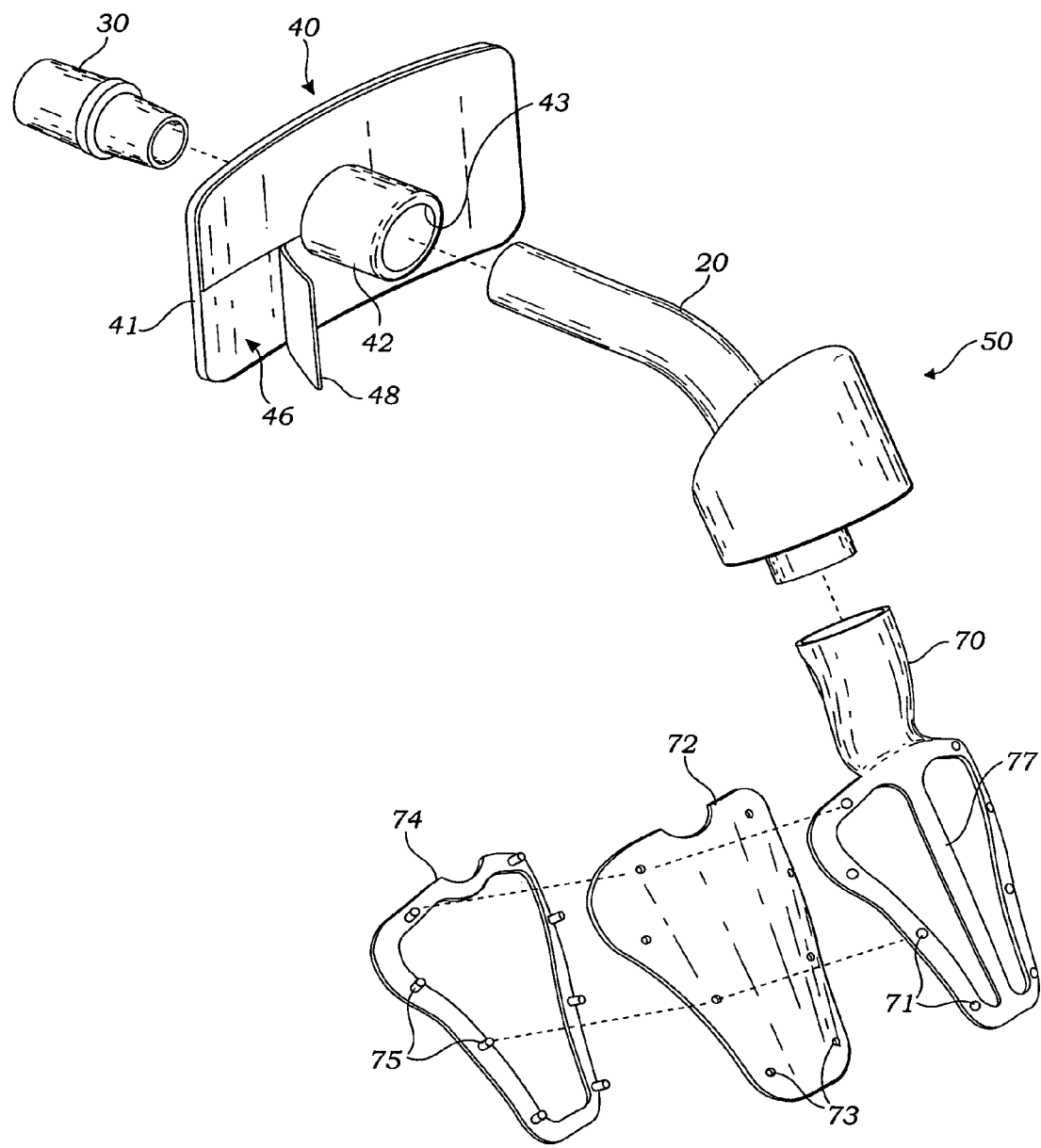
FIG. 3 is an exploded back perspective view thereof.
Figure 6:
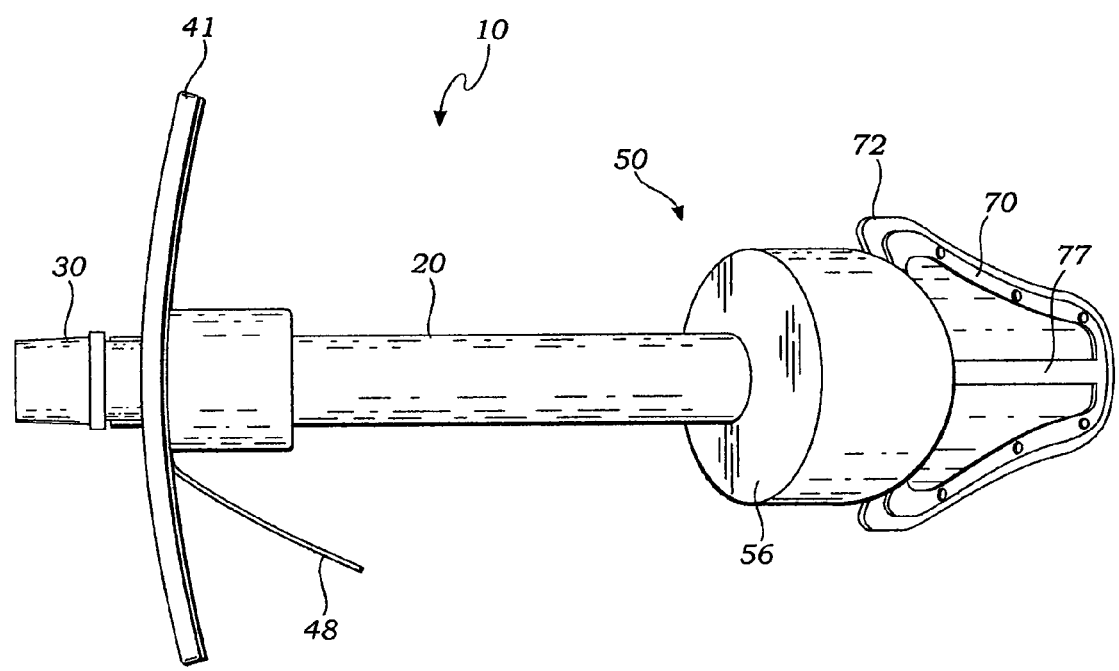
FIG. 6 is a top view thereof.
Figure 7:
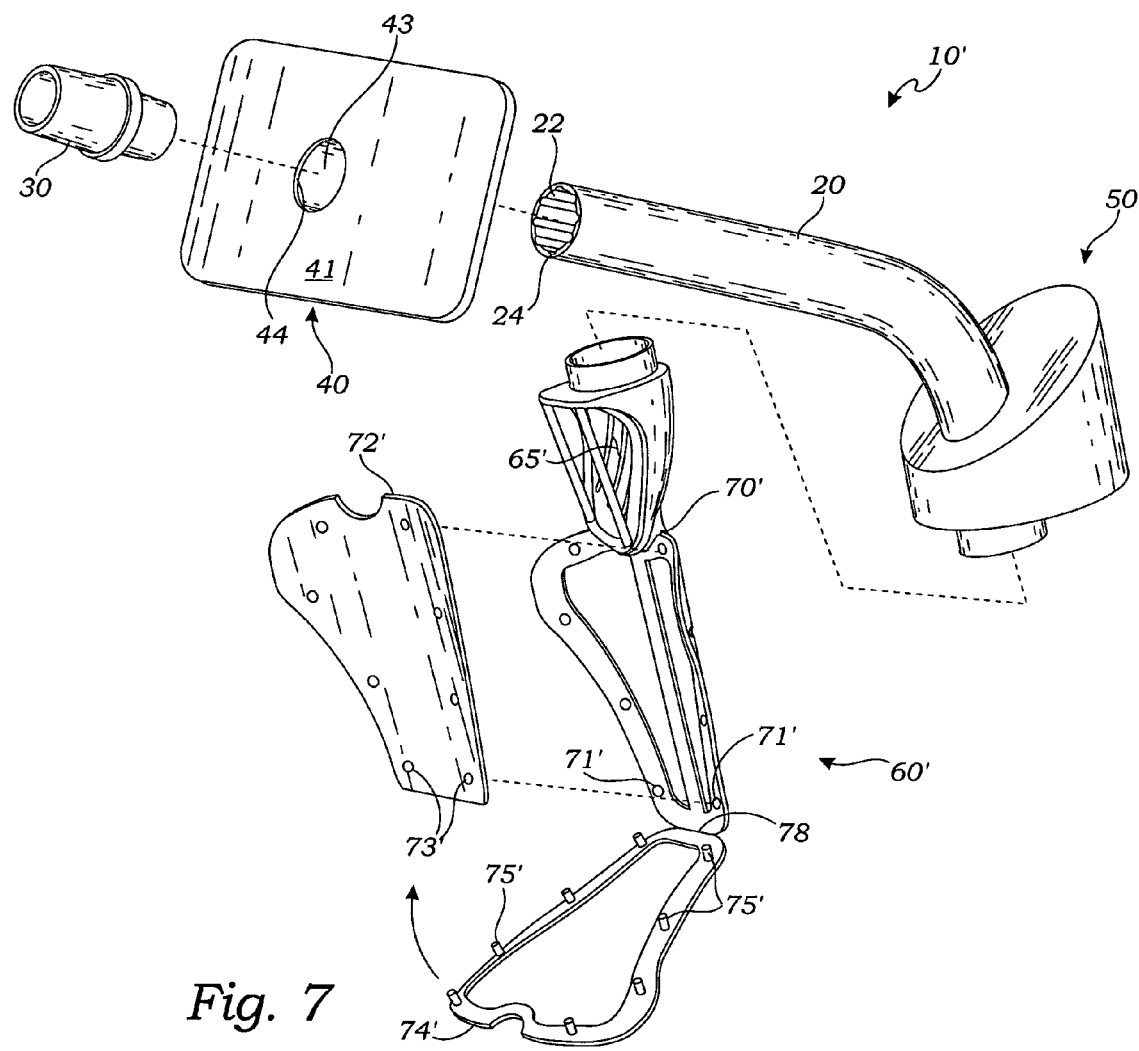
FIG. 7 is an exploded front perspective view of an alternative exemplary embodiment of the invention.

In more detail, referring now to FIGS. 2 and 3, it can be seen that the face plate assembly 40 is essentially comprised of a support plate 41 formed with a slight transverse curvature defining a somewhat concave distally-facing seal support surface corresponding to the typical adult facial structure, as best seen in FIG. 6, and a boss 42 extending distally and substantially perpendicularly from the support plate 41. While the support plate 41 is shown and described as having a particular size and configuration, it will be appreciated by those skilled in the art that a number of different shapes and curvatures are possible depending on various design considerations and the context in which the device 10 is to be used, whereby the substantially rectangular profile and particular transverse curvature shown and described are to be understood as merely exemplary, as will be further appreciated with reference to the alternative exemplary embodiment of FIGS. 12 and 13. Similarly, though the boss 42 is shown and described as being substantially annular and extending substantially perpendicularly, again, such structure is to be understood as being merely exemplary, such that the invention is not so limited. Rather, numerous other configurations and angles of the boss 42 are possible without departing from the spirit and scope of the invention, which will be further appreciated in connection with the below discussion relating to the device 10 in use. In the exemplary embodiment, the support plate 41 and boss 42 are molded as an integral unit from polypropylene, though it will be appreciated that other medical grade materials and methods of construction now known or later developed may be employed, wherein the support plate and boss may be formed as one unit or as two or more components assembled in a subsequent step. For example, it may be preferable in some applications to form the support plate 41 out of a relatively softer material such as polypropylene, polyethylene or polyurethane so as to be more comfortable on and more conforming to the particular patient's face, while it may be preferable for the boss 42 to be formed of a relatively harder material such as polycarbonate or acrylonitrile butadiene styrene ("ABS") so as to serve as a bite block or a means by which to prevent collapse of the tube, in the exemplary embodiment by way of the boss 42 forming an effective bite block between the incisors of the patient, and thereby preventing collapse of the tube in that region, when the device 10 is inserted into the patient's airway and the face plate assembly 40 is slid distally along the tube 20 so as to engage and substantially seal against or about the mouth of the patient, once again, as described in more detail below in connection with FIGS. 10 and 11. An opening 43 is formed as a bore passing through both the support plate 41 and the boss 42, such that it is through this bore 43 that the tube 20 slides. As shown in FIG. 7, an o-ring 44 may be seated within the bore 43 so as to seal around the outside diameter of the tube 20 as the face plate assembly 40 slides therealong, though it will be appreciated that any other sealing means now known or later developed may be employed, including but not limited to a net fit between the bore 43 and the outside surface of the tube 20 so as to not require an o-ring or the like. On the distally-facing surface of the support plate 41 a substantially tacky or somewhat sticky or adhesive sealing layer 46 is installed with an activation layer 48 thereover until use. When the device 10 is to be inserted, or at least before the face plate assembly 40 is advanced distally along the tube 20, the activation layer 48 is peeled back as shown and completely removed to expose the sealing layer 46. In the exemplary embodiment, the sealing layer 46 is formed from a hydrogel material, which material has a natural tackiness and may be further formed with an adhesive or tacky outer surface, additive or surface treatment to further facilitate sealing around the patient's mouth during use, as explained more fully below. Hydrogel is further known to have a natural sponginess so as to also provide comfort to the patient as the face plate assembly is brought into contact with the patient's mouth and surrounding facial anatomy. Those skilled in the art will appreciate that materials other than hydrogel, with or without added adhesives, any degree of sponginess, or an activation layer, whether now known or later developed, may be employed in the face plate assembly of the present invention without departing from its spirit and scope. Once the face plate assembly 40 is slidably installed on the tube 20 as shown, a standard 15 mm connector 30 is then mounted in the proximal end of the tube 20, as through a press fit, for connection to ventilation equipment or devices as is known in the art.

Figure 4:
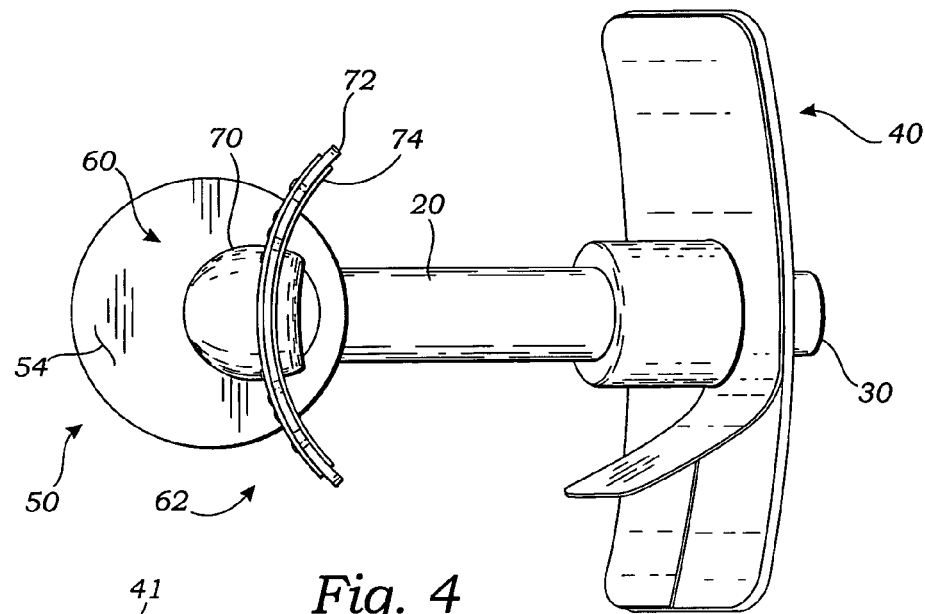
FIG. 4 is a bottom view thereof.

With continued reference to FIGS. 1-3, the exemplary embodiment of the introduction tip assembly 60 is again generally defined by the "arrowhead" lower frame portion 62 and the upper mounting portion 64, these portions being comprised of essentially three components: an installation frame member 70; a foam insert 72; and a keeper frame member 74. The installation frame member 70 is preferably formed as an integral single component constituting in part both the lower frame portion 62 and the upper mounting portion 64 of the introduction tip assembly 60, though those skilled in the art will appreciate that the mounting portion 64 and the installation frame member may be separate components. In order to form the lower frame portion 62, the foam insert 72 and the keeper frame member 74 are then installed on the installation frame member 70. In the exemplary embodiment, the installation frame member 70 is formed with a first fastener defined by two or more cross-holes 71, and the keeper frame member 74 is formed with a second fastener defined by two or more corresponding pins 75. Corresponding through-holes 73 are then formed in the foam insert 72, such that when the foam insert 72 is installed between the installation frame member 70 and the keeper frame member 74 the pins 75 pass through the through-holes 73 before seating in the cross-holes 71, whereby the foam insert 72 is substantially aligned and secured within the frame portion 62. The pins 75 may be of such a length and diameter as compared to the cross-holes 71 so as to be installed therein through a press fit, ultrasonic welding, solvent bonding, or any other such technique now known or later developed in the art. Ultimately, when the three components are brought together, the foam insert 72 is trapped between the opposite frame members 70, 74 to form the tip assembly 60 as shown. It will be appreciated by those skilled in the art that numerous other configurations of the frame members and foam insert, and the method of assembly thereof, are possible without departing from the spirit and scope of the invention, with or without the pinned connection shown and described, which is to be understood as merely exemplary. Whatever the particular configuration and assembly technique, it is preferred that the resulting introduction tip assembly 60, and the lower frame portion 62 particularly, be relatively smooth and atraumatic. For example, then, in the exemplary embodiment wherein the pins 75 are configured to pass through the foam insert 72 and into corresponding holes 71 in the installation frame member 70 and there be ultrasonically welded in place, any portion of the pins 75 extending beyond the installation frame member 70 would be melted down like rivets through the ultrasonic welding process and so be flush and atraumatic. Further, in the exemplary embodiment, the foam insert 72 defines an insert profile that is larger than a frame profile defined by the frame members 70, 74, so that in the resulting assembly the foam extends beyond the frame to yield a still more atraumatic introduction tip assembly 60 about its perimeter. Once more, those skilled in the art will appreciate that such an assembly can be achieved through a unitary construction or by bringing together a variety of components through mechanical means, as in the exemplary embodiment, or through insert molding, ultrasonic welding, thermal or chemical bonding, adhesion, or any other such suitable assembly method now known or later developed. Moreover, the frame portions 70, 74 may be formed as through an injection molding or other such process using any suitable medical grade material now known or later developed, including but not limited to polypropylene or polyurethane. The foam insert 72 itself is preferably formed of a hydrophilic or open cell foam material so as to be both relatively soft and also absorptive, such that in use, as explained further below, the tip, and the foam insert 72 specifically, can absorb gastric and other bodily secretions and so prevent or minimize the amount of such secretions entering the airway. An added benefit of this design is that as the foam 72 absorbs these secretions it will naturally expand, thereby only improving its seal within the cricopharynx. However, it is noted that the upper esophageal sphincter itself typically will hold at roughly 30 mm Hg pressure, so that because the typical patient is usually only ventilated to 20-25 mm Hg pressure, no seal in the cricopharynx is effectively needed when the introduction tip assembly 60 lodges in the upper end of the esophagus, or in the cricopharyngeal region. Accordingly, those skilled in the art will appreciate that the foam insert may be comprised in whole or in part of any number of foams, whether hydrophilic or hydrophobic, open or closed cell, or absorptive or non-absorptive. As best shown in the bottom view of FIG. 4, the frame portion 62 of the introduction tip assembly 60 is preferably formed with a lateral curvature substantially conforming to the upper esophageal anatomy. In order to meet the required mechanical properties of the introduction tip assembly 60 of effectively guiding the device 10 through the airway until it seats in the cricopharynx, and particularly to prevent "roll-up" during insertion, while allowing for a sufficient degree of exposed surface area of the foam insert 72, one or more lengthwise or axial bars or spines 77 may be formed in one or both of the frame members 70, 74. In the exemplary embodiment, a single lengthwise reinforcing spine 77 is formed in the installation frame member 70, as best shown in FIG. 3. The result is a tip assembly 60 comprised of a foam material for a substantial portion of its distal surface area while still having the appropriate structural integrity and performance.

Turning again to FIG. 1, the mounting portion 64 of the introduction tip assembly 60 further includes an opening generally denoted 65 that is in communication with the lumen 22 (FIG. 7) of the tube 20 when the tip assembly 60, and its mounting portion 64 specifically, is installed thereon, more about which is said below. As shown, the opening 65 may include one or more lengthwise channels 66 to reduce surface-to-surface contact, or friction, with any device being passed through the supraglottic airway device 10 into the trachea. The mounting portion opening 65 further defines a distal opening end 67 and a proximal opening end also defining the lip 68. Lateral posts 69 formed on opposite sides of the opening 65 in the mounting portion 64 and substantially interconnecting the distal and proximal opening ends 67, 68 cooperate with the lip 68 to keep the airway anatomy from obstructing the opening 65. It will be appreciated by those skilled in the art that numerous other configurations of the opening, the overhanging lip and the posts are possible without departing from the spirit and scope of the present invention and, accordingly, that the embodiment shown and described is merely for illustration.

Figure 5:
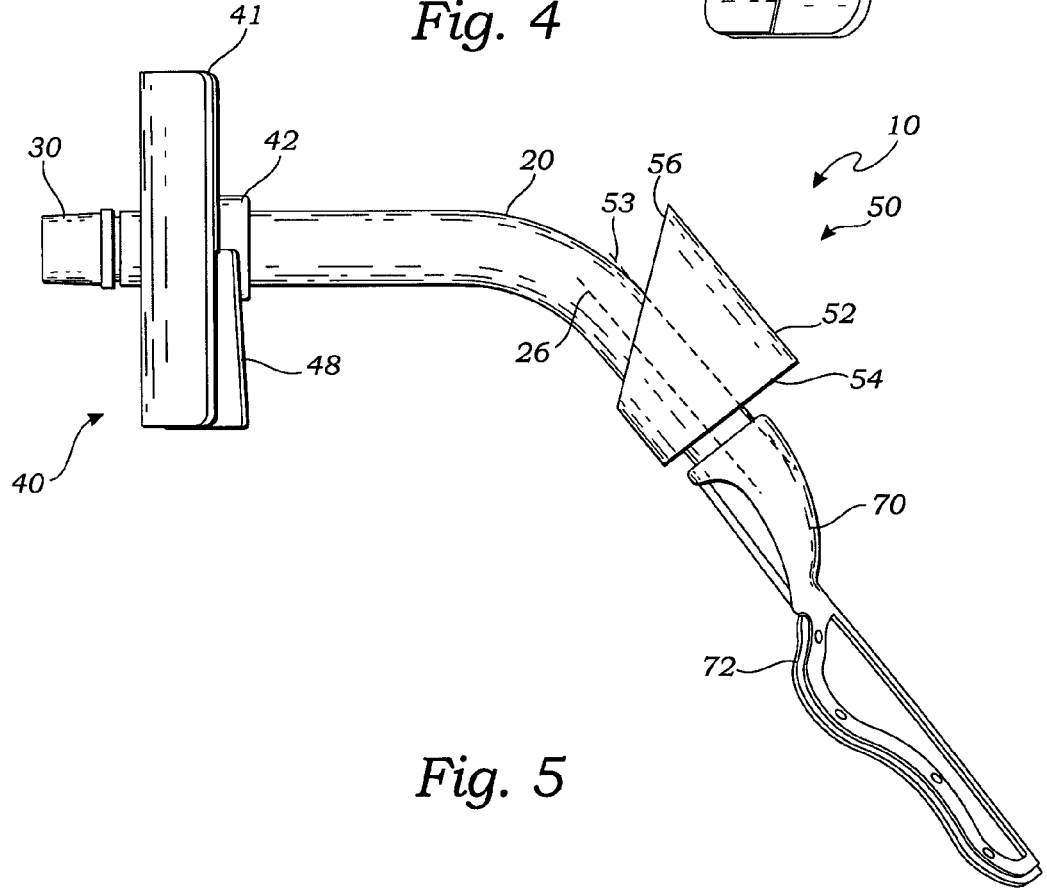
FIG. 5 is a side view thereof.

Referring now to FIG. 5, the expandable foam cuff 50 is installed on the tube 20 substantially at its distal end just above the introduction tip assembly 60, the cuff 50 being configured to seat within the pharynx when the device 10 is placed in the airway of the patient. In the exemplary embodiment, the foam material employed in the cuff 50 is a resilient, hydrophobic foam also known as a closed cell foam, a viscoelastic foam, or a slow recovery foam. A typical density of such a foam may be on the order of 7.9+/−1.0 lbs/ft$^3$. Those skilled in the art will appreciate that other medical grade foams may also be employed in the cuff 50 of the invention, including but not limited to absorptive, open cell foams whereby the cuff 50, like the foam insert 72 of the exemplary tip assembly 60, is able to absorb gastric, nasal or other bodily secretions, thereby keeping such away from the airway and potentially improving the airway seal at the same time. By being resilient, the foam cuff 50 is further advantageous in that it can simply be squeezed down before insertion and will then expand after the device 10 is in place to comfortably and effectively seal and anchor the device 10 within the pharynx without added steps relating to inflation, thereby functioning much like foam ear plugs or the like. More particularly, as best shown in FIG. 5, the cuff 50 comprises a substantially cylindrical body 52 having a lengthwise axis 53 and terminating distally in a distal cuff wall 54 that is substantially perpendicular to the axis 53 and terminating proximally in a proximal cuff 56 wall that is substantially oblique to the axis 53, whereby the cuff 50 is formed with a transverse cuff profile that is substantially trapezoidal. Furthermore, in the exemplary embodiment, the axis 53 of the cuff 50 is substantially parallel to and offset from the lengthwise centerline 26 of the tube 20, such that the cuff 50 itself is offset toward the rear of the anatomy in the orientation of the device 10 as it is inserted. The benefits of this cuff geometry will be best understood in conjunction with the below discussion relating to the device in use. While this configuration of the cuff 50 may represent a preferred embodiment, once more, those skilled in the art will appreciate that a variety of other configurations are possible within the scope and principles of the invention, depending on the context of use, the patient anatomy and other factors, so that the invention is not limited to the exemplary cuff design, which is to be understood as being merely illustrative. Ultimately, it will be appreciated that in use the cuff 50 anchors, locates and substantially seals device 10 within the patient airway. The cuff 50 is formed with a through-hole (not shown) that substantially corresponds to the outside diameter of the tube 20, whereby the cuff 50 is mounted on the tube 20 employing any appropriate means now known or later developed in the art, including solvent bonding, ultrasonic welding, over- or insert-molding, and a press or interference fit. Once the cuff 50 is so installed on the tube 20, the introduction tip assembly 60 may then be installed in the distal end of the tube 20 as shown. While a particular order of assembly has thus been described, those skilled in the art will appreciate that a number of assembly sequences and steps are possible in the present invention, depending on a variety of factors, such that the invention is not so limited. For example, the introduction tip assembly 60 may be installed on the tube 20 first, then the cuff 50, next the face plate assembly 40, and finally the connector 30. Again, the face plate assembly 40 and the tip assembly 60 may themselves be made up of subcomponents such that each is first assembled as a subassembly before then being installed on the tube in any particular sequence, or the face plate and tip assemblies may, in fact, in other embodiments be actually formed as single components, depending on the particular application.

Turning to FIG. 7, there is shown an alternative exemplary embodiment of the supraglottic airway device 10' of the present invention. For the purpose of illustration, the device 10' remains the same in all respects as that of FIGS. 1-6, except for the introduction tip assembly 60'. Here, the upper and lower portions, or the mounting portion and the frame portion, of the tip assembly 60' are formed as a single molded article with the installation frame member 70' and the keeper frame member 74' connected along their distal edge by a living hinge 78. Otherwise, the installation and keeper frame members 70', 74' are in this alternative exemplary embodiment much the same as those of the first exemplary embodiment of FIGS. 1-6, including the pins 75' on the keep frame member 74' configured to pass through through-holes 73' in the foam insert 72' and engage corresponding cross-holes 71' formed in the installation frame member 70'. Those skilled in the art will appreciate that the foam insert 72' must be slightly shorter than its counterpart insert 72 of the embodiment of FIGS. 1-6 in order to accommodate the living hinge 78. Accordingly, it will be further appreciated that in this alternative embodiment of the device 10', the leading edge of the tip assembly 60' will be the living hinge 78, or the material from which the frame members 70', 74' are integrally molded, rather than the foam insert 72'. As such, the foam insert 72' will extend beyond the lateral edges of the frame, but not the distal end, and so in the alternative embodiment does not account for the entire perimeter of the frame. Nevertheless, those skilled in the art will appreciate that the formation of the frame members together about a living hinge, and the transition of this living hinge to the sides of the frame members and then to the laterally-extending foam will still result in an atraumatic introduction tip while effectively reducing the number of components in the assembly and inherently furthering the integrity of the introduction tip assembly 60'.

With continued reference to FIG. 7, in this exploded view the construction of the tube 20 is best seen and understood. The tube 20 is formed with an interior lumen 22 that communicates from one end of the tube to the other. When the device 10' is fully assembled, it will be appreciated that the lumen 22 then communicates or creates a passage between the connector 30 at the proximal end of the device 10' and the introduction tip assembly 60', and the opening 65' specifically, at the opposite distal end of the device 10', whereby when the device 10' is in use air may pass from a ventilation system or apparatus connected to the connector 30 through the lumen 22 and the opening 65' into the patient airway, and vice versa. Thus, the supraglottic airway device 10' creates an artificial airway within the patient through which positive pressure ventilation and other medicines can be imparted to the patient. Moreover, other devices such as endotracheal tubes may also be passed through the lumen 22 of the airway device 10' and into the patient's trachea. In order to minimize the surface-to-surface or frictional contact between an endotracheal tube or other such device being passed (not shown) and the inside wall of the lumen 22, as shown, a plurality of lengthwise striations 24 may be formed along the lumen 22. These striations 24 reduce the actual surface area of the lumen wall and thereby reduce friction with anything being passed therethrough. The striations also act as smaller air passages through which the patient may still be ventilated even while another device is located within the lumen 22, such that a secondary lumen within the tube 20 is not required. In the exemplary embodiment, the tube 20 is an extruded polyvinyl chloride ("PVC") with the striations 24 being on the order of 0.060" deep. The pre-formed bend of the tube may be formed in a secondary operation. It will be appreciated by those skilled in the art that a variety of materials for the tube and configurations of the tube in terms of length, diameter, size and number of striations, if any, and perform of one or more bends are possible in the present invention without departing from its spirit and scope.

Figure 8:
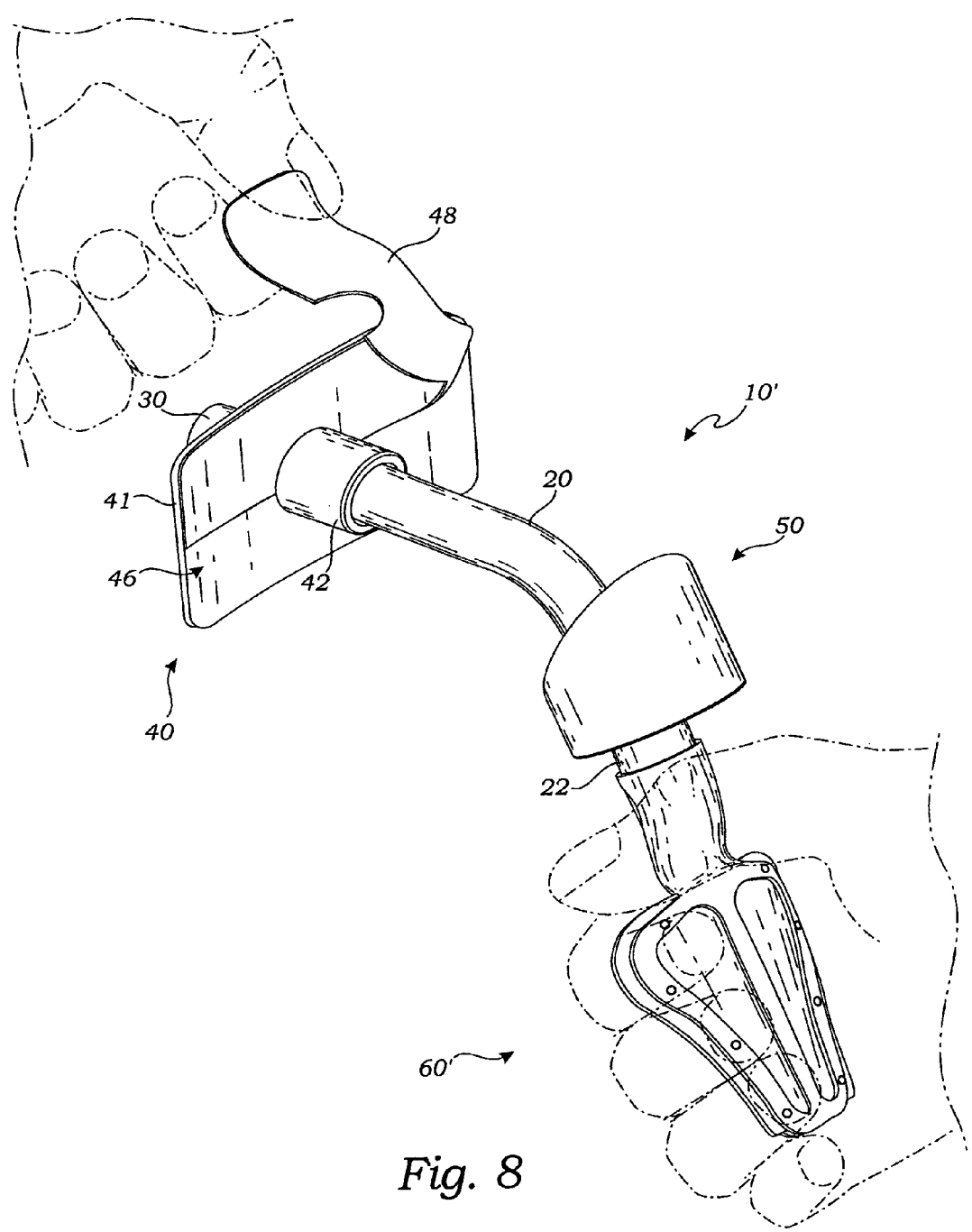
FIG. 8 is a rear perspective view thereof showing the device in a first step of preparation for use.
Figure 9:
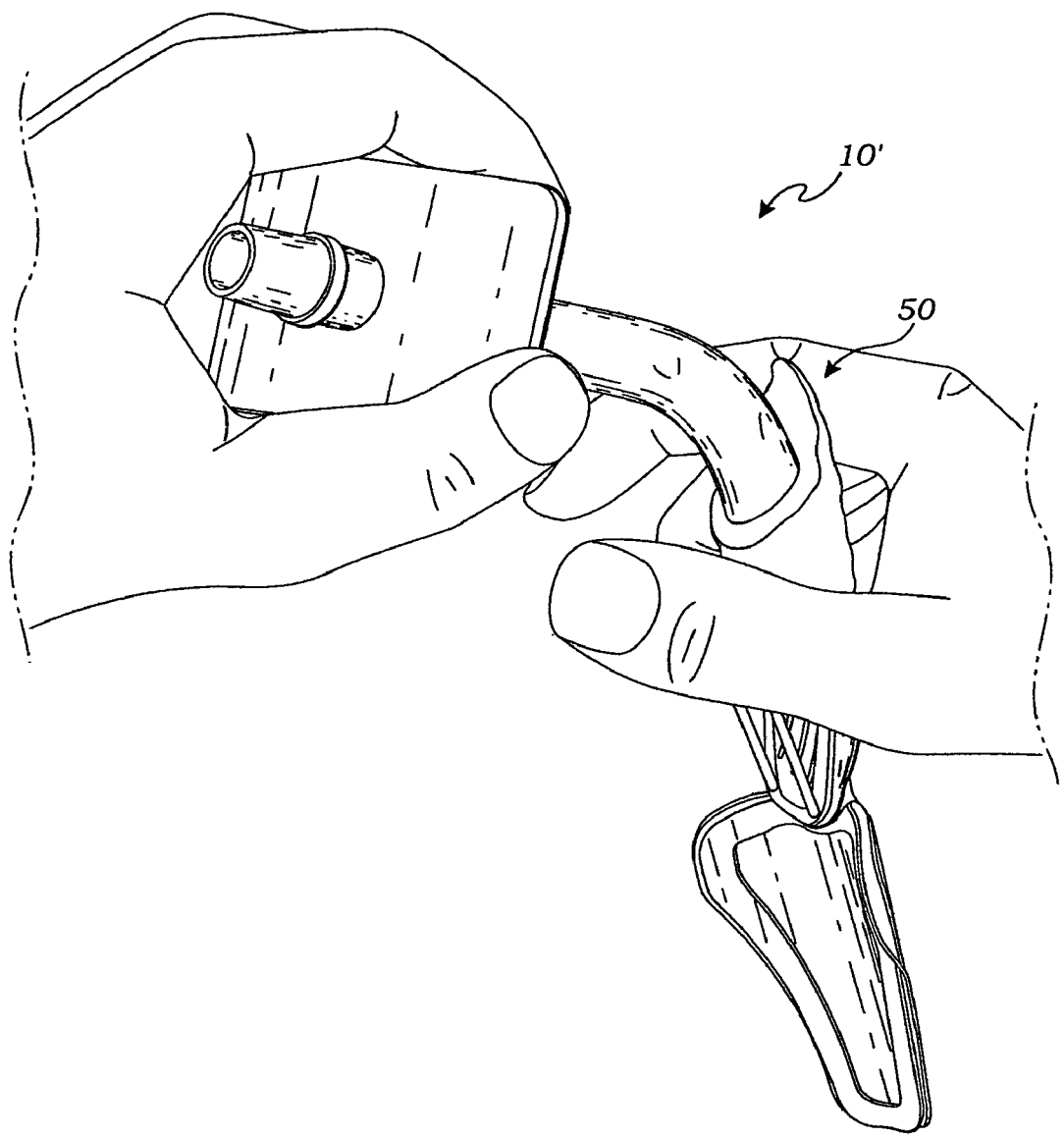
FIG. 9 is a front perspective view thereof showing the device in a second step of preparation for use.

Referring now to FIGS. 8 and 9, there is shown the alternative embodiment supraglottic airway device of FIG. 7 being prepared for use in essentially two steps. Those skilled in the art will appreciate that these same steps would apply to the exemplary embodiment device 10 of FIGS. 1-6 or any other such device according to the principles of the present invention. First, as shown in FIG. 8, the device 10', after being removed from its sterile packaging (not shown), is grasped about the introduction tip assembly 60', as shown, the cuff 50 and/or the tube 20 with one hand while with the other hand the user peels away the activation layer from the support plate 41 of the face plate assembly 40 to reveal the sealing layer 46 of hydrogel or the like. The activation layer 48 is completely removed and discarded. Next, as shown in FIG. 9, the user now grasps and squeezes the expandable foam cuff 50 to temporarily compress the cuff about the tube 20 (FIG. 8). The supraglottic airway device 10' is now ready for insertion into the patient airway. Additionally, though, as is known in the art, the tip, tube and/or cuff may be lubricated to further ease insertion. It will be appreciated by those skilled in the art that these prepatory steps can be taken in any order and by grasping and manipulating the device in a number of ways, such that the identified steps and order thereof are to be understood as merely exemplary.

Figure 10:
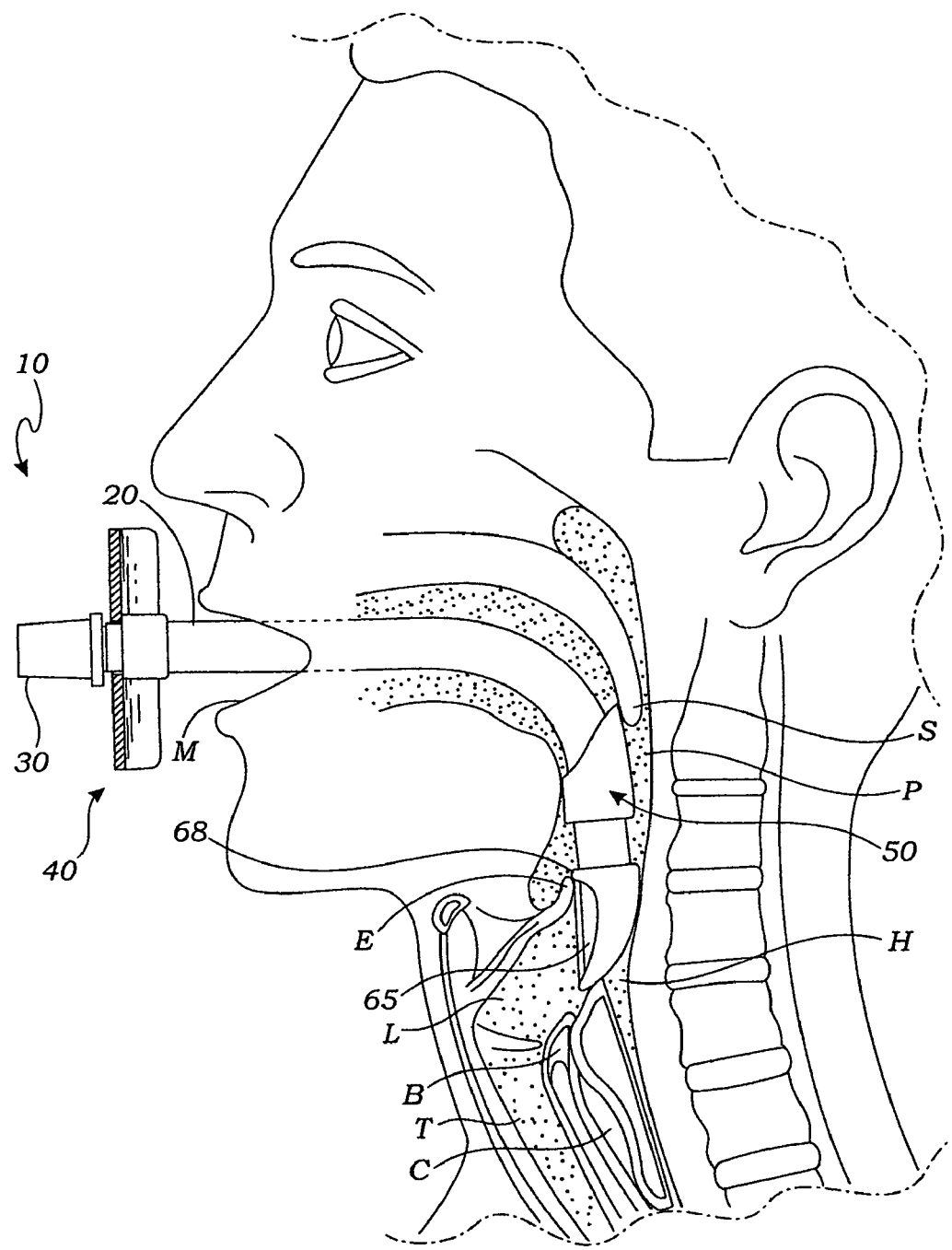
FIG. 10 is a side schematic view, partially in section, showing the device in a first phase of use.
Figure 11:
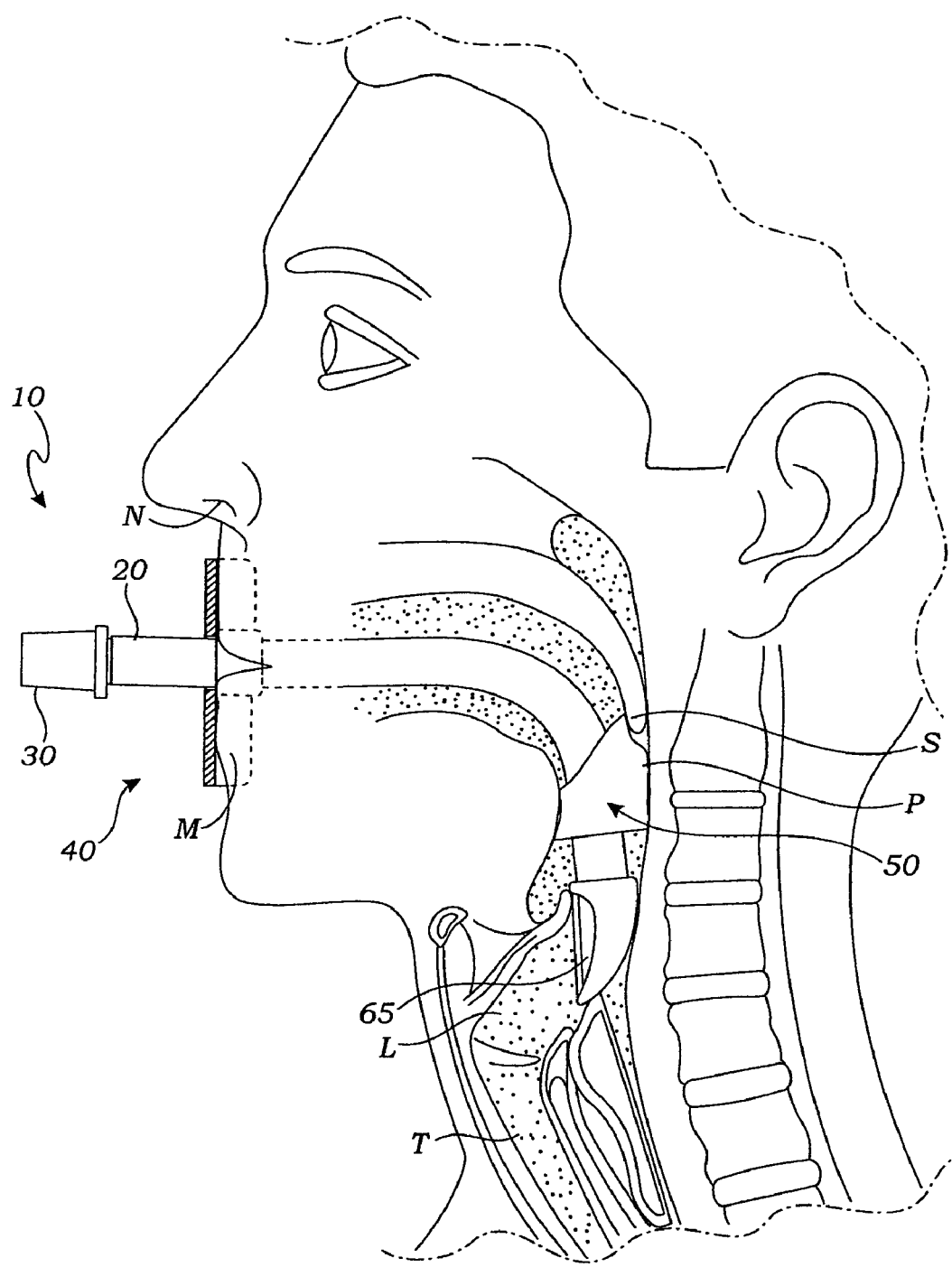
FIG. 11 is a side schematic view, partially in section, showing the device in a second phase of use.

Turning now to FIGS. 10 and 11, as read in light of FIGS. 1, 2 and 7, the supraglottic airway device 10 of the present invention is shown within the patient airway in effectively two stages of operation. In FIG. 10, the device 10 has been prepared as described above in connection with FIGS. 8 and 9 and inserted into the patient airway by essentially allowing the introduction tip assembly 60 to follow the hard and soft pallet in the back of the airway down through the upper part of the pharynx P, or the oropharynx, through the intermediate pharyngeal area commonly denoted the hypopharynx H or laryngopharynx, and into the cricopharynx C, where the lower frame portion 62 of the tip assembly 60 seats, thereby positioning the mounting portion 64, and the opening 65 particularly, adjacent the larynx or laryngeal inlet L, which leads through the vocal cords to the patient's trachea T. As can be seen, the lip 68 and bars 69 formed on the upper mounting portion 64 of the introduction tip assembly 60 substantially about or adjacent to the opening 65 serve to keep the epiglottis E and other parts of the airway anatomy away from the opening 65 so as to not partially or wholly occlude the artificial airway. To facilitate this positioning of the device 10 with respect to the anatomy, it may be beneficial in practice to advance the device 10 slightly farther than necessary and then pull back on the device 10 slightly to more fully displace the anatomy about the opening 65. Those skilled in the art will appreciate that the "arrowhead" or wedge shape of the tip assembly's frame portion 62, including its laterally concave curvature, will not only seat the device properly within the cricopharynx, but will also be effectively prevented from over insertion by virtue of this shape and the engagement of the wider part of the frame portion and/or the lower opening end 67 of the upper mounting portion 64 with the cricoid bone B. As can be seen in FIG. 10, with the device 10 so inserted, immediately thereafter the foam cuff 50 remains in its compressed state, such that the pharynx P, and the nasopharynx particularly, is not yet sealed. Referring now to FIG. 11, once the device 10 is properly positioned within the airway, the face plate assembly 40 is then slid distally over the tube 20 until the exposed sealing material 46 on the distally-facing concave surface of the support plate 41 is brought into contact with the patient's mouth M and surrounding facial anatomy so as to effectively seal the oropharynx. In an exemplary technique, the user may advance the face plate assembly 40 with one hand while stabilizing the device by grasping the tube 20 and/or connector 30 with the other hand. A strap, medical tape or other such device (not shown) may be employed to hold the face plate assembly in position. Meanwhile, the self-expanding foam cuff 50 has gradually been returning from its compressed "prep" state, as shown in FIG. 9, toward its natural uncompressed state, as shown in FIGS. 1-8. The resiliency of the foam material allows the cuff not only to have a "memory," and thus a predisposition toward its formed shape, but also the quality of substantially conforming to the anatomy rather than requiring the anatomy to conform to the cuff, as is more the case with inflation cuffs. Thus, as shown in FIG. 11, the foam cuff 50 will continue to expand until it presses against and conforms to the airway anatomy, particularly the pharyngeal area P, whereas the soft pallet S is also pushed to the back of the airway to cooperate with the cuff in substantially sealing at least the nasopharynx. Those skilled in the art will appreciate that configuring the cuff 50 as in the exemplary embodiment to have a substantially trapezoidal profile, with the larger side offset toward the back of the airway anatomy as shown, further facilitates this sealing effect. The expansion of the cuff 50 within the pharynx P serves to substantially seal the oropharynx as well, though it will be appreciated that this is not necessary since the oropharynx is substantially sealed by the face plate assembly 40 against the mouth M of the patient. Therefore, in the exemplary embodiment, the oropharynx is effectively sealed twice, making a successful intubation and positive pressure ventilation all the more likely or consistent with the device of the present invention, again, without the additional time and risk involved with the typical inflation cuff. As such, it will be further appreciated that even were the cuff 50 not to completely seal the pharynx after fully expanding, it nevertheless serves the additional purpose of locating and seating or anchoring the device 10 within the airway. Though not shown, those skilled in the art will also appreciate that the distally protruding boss 42 of the face plate assembly 40 serves as a "bite block," the term "bite block" being used loosely for any material or element or portion thereof that is positioned between the teeth of the patient, here the incisors, in order to prevent or discourage collapsing the tube 20. In an alternative exemplary embodiment, one or more relatively longer protrusions from the support plate could extend to a location between the molars so as to prevent closure of the patient's mouth and thereby prevent collapsing the tube 20. Those skilled in the art will appreciate that with the patient so intubated with the supraglottic airway device 10 of the present invention, a direct-access airway is created from the connector 30 through the lumen 22 of the tube 20, through the opening 65 of the introduction tip assembly 60, and into the larynx and trachea, relatively quickly, easily and atraumatically and with minimal secretions later entering the airway as a result of the hydrophilic foam most likely at least employed in the introduction tip assembly. Once again, then, with the airway device 10 so inserted, a ventilator, respirator, bag, or other such ventilation device can be connected to the connector 30 so as to ventilate the patient in any manner now known or later developed in the art. Moreover, before or after such ventilation has taken place, any such ventilation device may be temporarily removed so as to pass an endotracheal tube (not shown) or the like through the inside lumen 22 and the opening 65 of the supraglottic airway device 10 and through the larynx L and vocal cords into the trachea T. Again, were it necessary to immediately ventilate the patient before removal of the supraglottic airway device but while the endotracheal tube or other such device is passed therethrough, any ventilation device can once more be connected to the connector 30 and air passed into the patient's airway through the striations 24 in the lumen 22 of the tube 20, which striations thus effectively serve as a secondary lumen. When the supraglottic airway device 10 is removed, as when an endotracheal tube is intubated or the patient is simply no longer in need of respiratory assistance, the device 10 is preferably discarded as a single use device, though those skilled in the art will appreciate that with the appropriate medical grade materials, the device 10 may also be re-sterilized and re-used multiple times. It will be appreciated that while a particular sequence of use and its resulting benefits have been described, numerous other uses and derived functionality may be accomplished with the supraglottic airway device of the present invention depending on the clinical application.

Figure 12:
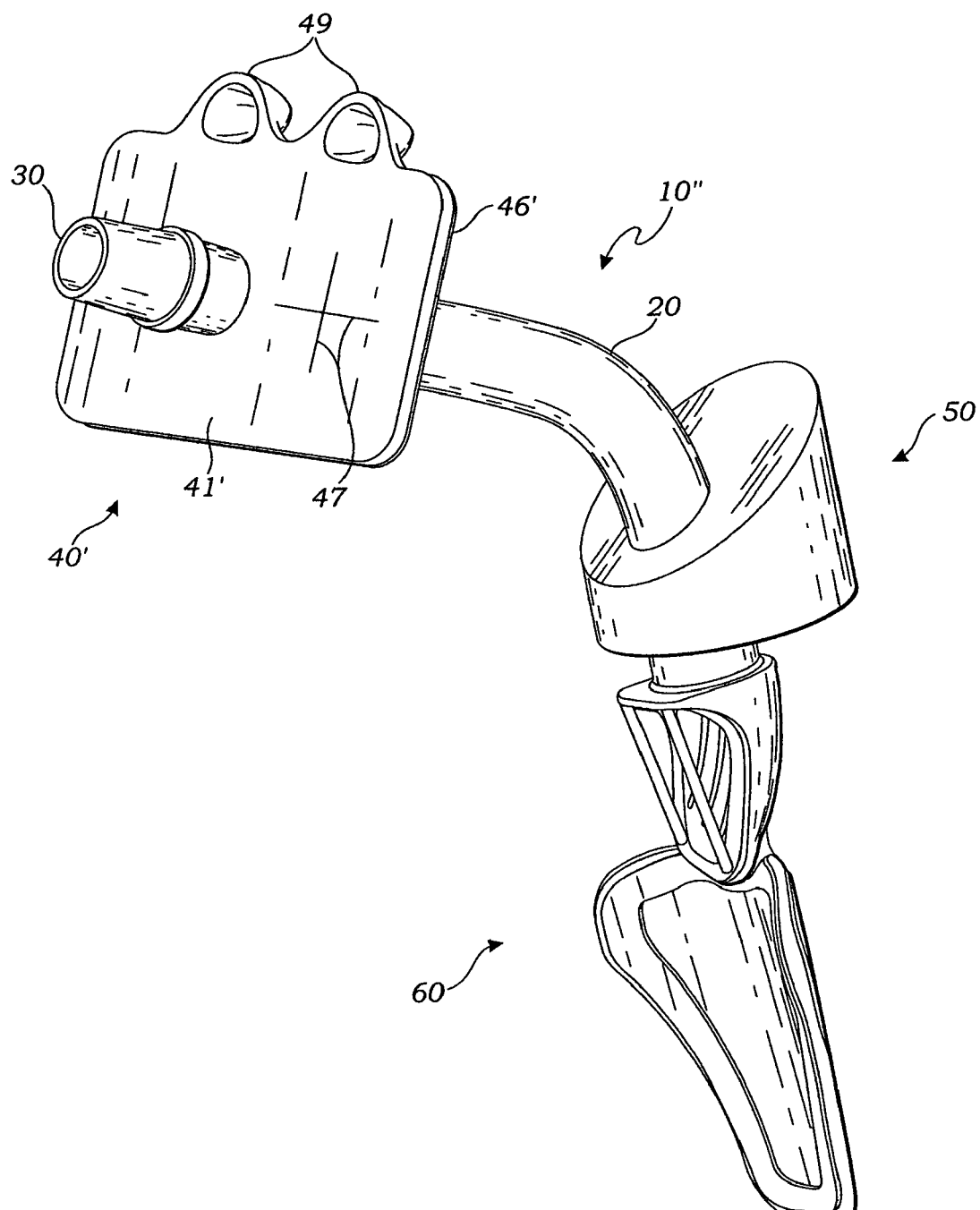
FIG. 12 is a front perspective view of an alternative exemplary embodiment of the invention.
Figure 13:
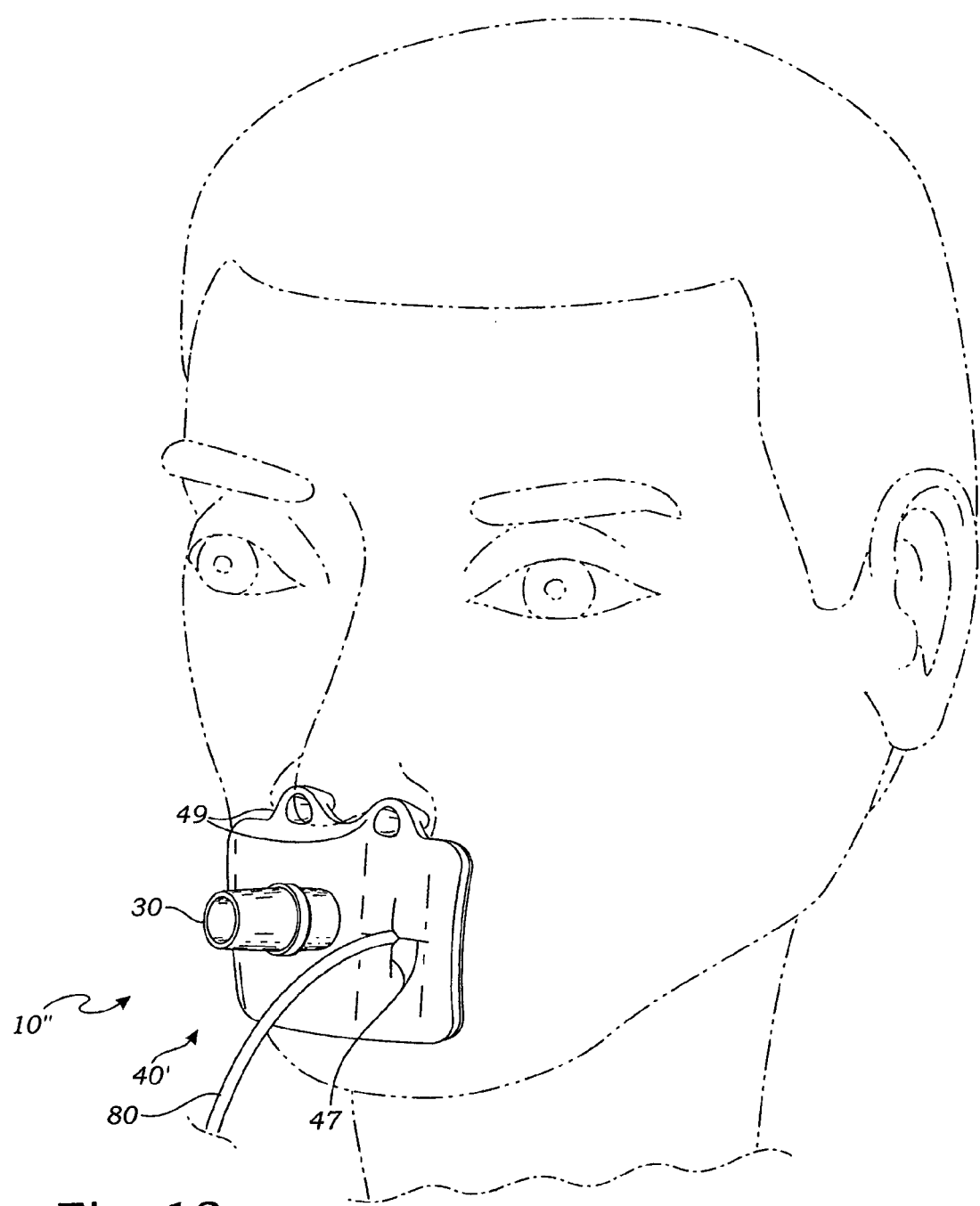
FIG. 13 is a front perspective view thereof in use.

Referring now to FIGS. 12 and 13, yet another exemplary embodiment of the supraglottic airway device 10" of the present invention is shown. For the purpose of this illustration, the device remains essentially the same as that of FIGS. 1-6, only now including a modified face plate assembly 40'. Here, the support plate 41' is formed with two tabs 49 along its top edge substantially corresponding in location and size and shape to the nostrils of the patient. In the alternative exemplary embodiment, the tabs 49 are configured as distally-tapered plugs formed integral with the support plate 41' so as to extend distally therefrom in the direction of the patient, and the patient's nostrils, specifically. As shown, the hydrogel or other such sealing layer 46' located on the distal surface of the support plate 41' extends up onto and about the distal surface of the nose tabs 49 to facilitate comfort and sealing in the nostrils when the face plate assembly 40' is advanced distally as explained above in connection with FIG. 11. In the exemplary alternative embodiment, the sealing layer 46' may be ⅛" to ¼" thick so as to provide further comfort and accommodate sealing within various nostril anatomies. Thus, as shown in FIG. 13, tabs 49 effectively plug the nose of the patient during use, thereby sealing the nasopharynx. As a result, as noted above in connection with the double-seal of the oropharynx achieved by the combination of the face plate assembly 40 and cuff 50, so here an effective double-seal of the nasopharynx is also effectively achieved by the combination of the face plate assembly 40' and cuff 50. Accordingly, those skilled in the art will appreciate that the alternative face plate assembly 40' seals about the mouth and the nose and thereby adds an additional factor of safety for establishing an artificial airway in a patient for the purpose of positive pressure ventilation. Moreover, in particular cases and for a variety of reasons, it will be further appreciated that the cuff 50 may be removed altogether and a substantially effective seal of the oro- and nasopharynx achieved through the alternative exemplary face plate assembly 40' alone. Those skilled in the art will also appreciate that while a particular configuration of nose tabs 49 is shown and described, the invention is not so limited, but instead the tabs may take a number of configurations sufficient to substantially plug the nostrils, whether integral with the support plate or formed separately and then installed on the device using any means now known or later developed. As a further alternative, rather than the tabs 49, a nose clip (not shown) as is known and used in the art may be molded to or otherwise mounted on or incorporated with the support plate, such as by a living hinge or the like, in order to separately seal the nose and hence the nasopharynx. With continued reference to FIGS. 12 and 13, there is also shown one other additional feature in the alternative face plate assembly 40': one or more slits 47 formed in the support plate 41'. These slits 47 effectively provide a means for passing other devices into the airway without removing the supraglottic airway device 10" or even retracting the face plate assembly 40' or otherwise breaking the seal about the patient's mouth or nose. It will be appreciated by those skilled in the art that the combination of a polypropylene or similar material for the support plate 41' with a hydrogel or like material as the seal layer 46' on the distal or patient side of the support plate effectively creates a self-sealing opening through the face plate. That is, such a "crosshairs" two-slit opening as shown would essentially be capable of allowing relatively small diameter devices 80 such as Yankauer suction catheters to be passed therethrough while still substantially sealing about the device 80. In this way, the airway could be suctioned or monitored without compromising the airway or the ability to ventilate the patient. Then, when the device 80 is removed, the slits 47 would naturally close and effectively self-seal so as to provide continued integrity of the artificial airway. Those skilled in the art will appreciate that the number and arrangement of such slits 47 or other selectively openable passages through the face plate may vary without departing from the spirit and scope of the invention and, accordingly, that the embodiment of FIGS. 12 and 13 is merely exemplary.

In sum, the supraglottic airway device of the present invention is capable of conveniently, safely and effectively establishing an airway in a patient by sealing both the oropharynx and nasopharynx, and particularly about the mouth and/or the nose by means of a novel face plate assembly slidably installed on the device's tube, while also blocking and/or absorbing gastric and nasal secretions. As such, and further by way of an expandable foam cuff, the supraglottic airway device can achieve the necessary positioning within the pharynx without significant mucosa pressure, potentially increasing patient acceptance of the device and reducing the amount and severity of drugs and local paralyzing agents needed to achieve a safe and effective intubation. This may lead to relatively more successful intubations with fewer side effects for the patient, thereby also saving significant costs per procedure both due to the fewer drugs and the reduced post-intubation intervention and recovery time.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor believes that the claimed subject matter is the invention.

What is claimed is:

1. A supraglottic airway device comprising:
a tube having an interior lumen; and an introduction tip assembly mounted on the tube substantially at one end thereof, the introduction tip assembly comprising a mounting portion connected to the tube and having an opening therein configured to communicate with the lumen, and the introduction tip assembly further comprising a frame portion extending substantially distally from the mounting portion and having a foam insert installed thereon, whereby the introduction tip assembly guides the device into the airway of a patient and substantially locates within the hypopharynx such that the frame portion substantially seats within the cricopharynx and the foam insert thereof absorbs bodily secretions; wherein the frame portion further comprises an installation frame member integral with the mounting portion and having a first fastener; and a keeper frame member having a second fastener configured to engage the first fastener, wherein the foam insert is secured within the frame portion between the installation frame member and the keeper frame member.

2. The device of claim 1 wherein:
the first fastener comprises at least two cross-holes formed within the installation frame member; the second fastener comprises at least two pins configured to engage the cross-holes, wherein the foam insert is formed with through-holes through which the pins pass when the foam insert is installed between the installation frame member and the keeper frame member, whereby the foam insert is substantially aligned and secured within the frame portion.

3. The device of claim 1 wherein the installation frame member and the keeper frame member are formed as separate components, each having a frame profile that is substantially the same; and
the foam insert is configured having an insert profile substantially larger than the frame profile, whereby the foam cuff forms the entire perimeter edge of the frame portion.

4. The device of claim 1 wherein the installation frame member and the keeper frame member are formed as a single component interconnected along a distal edge by a living hinge.

5. The device of claim 1 wherein the installation frame member is formed with a lengthwise reinforcing spine.

6. The device of claim 1 wherein: the opening in the mounting portion has a distal opening end and a proximal opening end; the mounting portion is further configured with a lip projecting substantially outwardly from the proximal opening end; and lengthwise posts are formed about the opening in the mounting portion substantially interconnecting the lip and the distal opening end, whereby the posts cooperate with the lip to discourage the airway anatomy from occluding the opening when the device is positioned in the airway of the patient with the introduction tip assembly located substantially within the hypopharynx.

7. The device of claim 1 wherein: the installation frame member and the keeper frame member are formed of a material selected from the group consisting of polypropylene and polyurethane; and the foam insert is formed of an open cell foam material.

* * * * *